US008588915B2

(12) United States Patent
Iyer et al.

(10) Patent No.: US 8,588,915 B2
(45) Date of Patent: Nov. 19, 2013

(54) ELECTRONIC MODULE ASSEMBLY FOR FILTERED FEEDTHROUGHS

(75) Inventors: Rajesh V. Iyer, Eden Prairie, MN (US); Lea A. Nygren, Bloomington, MN (US); Stephanie L. McCracken, Minneapolis, MN (US); Mukul Jain, Woodbury, MN (US); Christine Gale Kronich, Saint Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 598 days.

(21) Appl. No.: 12/750,702

(22) Filed: Mar. 30, 2010

(65) Prior Publication Data
US 2010/0249861 A1    Sep. 30, 2010

Related U.S. Application Data

(60) Provisional application No. 61/165,314, filed on Mar. 31, 2009.

(51) Int. Cl.
*H01G 4/35* (2006.01)
*A61N 1/00* (2006.01)

(52) U.S. Cl.
USPC .............. 607/37; 607/36; 361/302; 333/182; 439/909

(58) Field of Classification Search
USPC .................... 607/32, 36, 37, 2, 5, 9; 333/182; 439/909, 688, 669, 722, 620.01, 174; 361/302
See application file for complete search history.

(56) References Cited

U.S. PATENT DOCUMENTS

| 5,905,627 | A | 5/1999 | Brendel et al. | |
|---|---|---|---|---|
| 6,768,629 | B1 | 7/2004 | Allen et al. | |
| 2003/0069612 | A1 | 4/2003 | Zart et al. | |
| 2005/0274384 | A1* | 12/2005 | Tran et al. | 128/831 |
| 2007/0043399 | A1* | 2/2007 | Stevenson et al. | 607/37 |
| 2007/0179551 | A1 | 8/2007 | Iyer et al. | |
| 2007/0179554 | A1* | 8/2007 | Iyer et al. | 607/37 |
| 2009/0080140 | A1* | 3/2009 | Iyer et al. | 361/302 |

FOREIGN PATENT DOCUMENTS

| WO | WO 2007/087487 | 8/2007 |
|---|---|---|
| WO | WO 2008/103166 | 8/2008 |

OTHER PUBLICATIONS (PCT/US2010/029340) PCT Notification of Transmittal of the International Search Report and the Written Opinion of the International Searching Authority.
(PCT/US2010/029345) PCT Notification of Transmittal of the International Search Report and the Written Opinion of the International Searching Authority.

* cited by examiner

*Primary Examiner* — Christopher D Koharski
*Assistant Examiner* — Pamela M Bays
(74) *Attorney, Agent, or Firm* — Carol F. Barry

(57) ABSTRACT

An electronic module assembly (EMA) for an implantable medical device is disclosed. The EMA comprises a non-conductive block having a top side, a bottom side, a front side and a back side. A plurality of conductive strips are coupled to the non-conductive block. Each conductive strip possesses a front side and a back side. The back side of each conductive strip extends from the front side across the top side and over to back side of the non-conductive block.

19 Claims, 12 Drawing Sheets

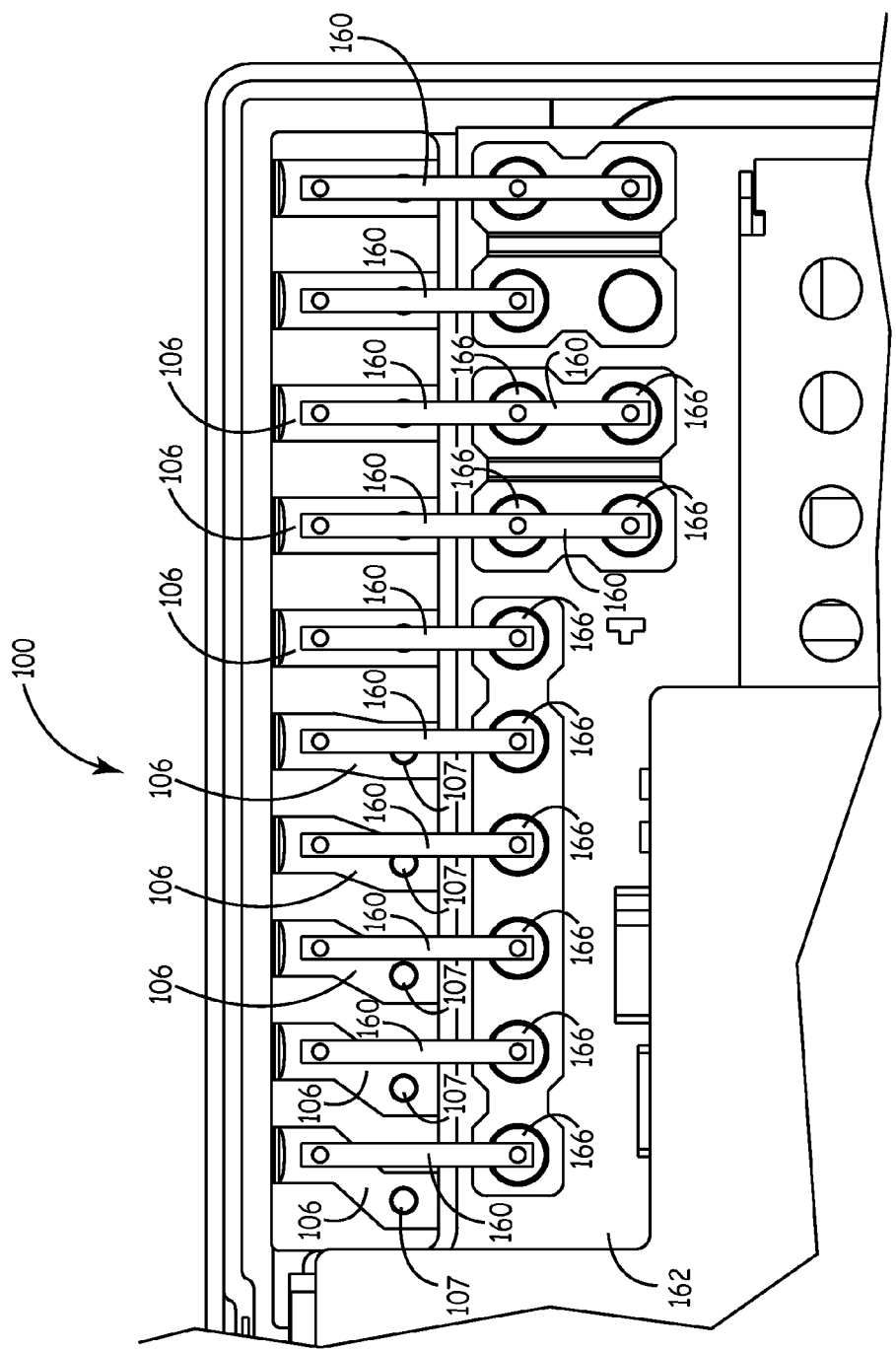

ELECTRONIC MODULE ASSEMBLY FOR FILTERED FEEDTHROUGHS

CROSS-REFERENCE TO RELATED APPLICATIONS

This application claims the benefit of U.S. Provisional Application No. 61/165,314, filed on Mar. 31, 2009. The disclosure of the above application is incorporated herein by reference.

TECHNICAL FIELD

The present disclosure relates generally to implantable medical devices, and, more particularly, to an electronic module assembly that includes contact pads for connecting feedthrough pins to a hybrid assembly.

BACKGROUND

Implantable medical devices (IMDs) typically include a housing that encloses a variety of internal components, and protects the components from an implanted environment. For example, within the human body, the housing is sealed to prevent introduction of fluids or moisture to the internal components. In many cases, the implantable medical device includes external components that extend outside of the housing and communicate with the internal components.

One example is an implantable cardioverter/defibrillator (ICD), which includes an internal battery, at least one charging capacitor, and electronic circuitry. The electronic circuitry typically is coupled to pacing and/or diagnostic leads that extend outside of the device housing for positioning within or near the targeted tissue such as the heart. To protect internal components while permitting electrical connections with external components, the ICD includes a connector module connected to a filtered feedthrough electronic module assembly (FFEMA). The connector module is electrically connected to circuitry inside a sealed case of the implantable medical device through one or more feedthrough pins extending from the FFEMA. FFEMA comprises an electronic module assembly (EMA) connected to a feedthrough assembly via laser welding of the feedthrough pins to the conductive strip on the EMA. The EMA is composed of an electronic module block with a set of conductive strips located solely at one end of the EMB. To ensure that a high quality EMB has been manufactured, a testing device with a set of pogo pins verifies that the conductive strips function properly. In some cases, the pogo pins may contact the conductive strips more than once, which may remove a portion of a conductive plating on the conductive strips. A current is then passed through the pogo pins to test whether the conductive strips function. Pogo pins may scratch, nick or gouge the gold/platinum plated surface of the conductive strips, which may not permit a reliable connection of the hybrid circuit to the EMB via laser ribbon bonding/wire bonding/parallel gap welding process to the conductive strip of the EMB.

Efforts to simplify or reduce the complexity, cost, and time of the manufacturing and assembly process can directly impact the cost of the implantable medical device for patients. Accordingly, more simple and cost-effective device assembly processes for implantable medical devices are desirable.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 3C is a schematic cutaway view of the FFEMA depicted in FIGS. 3A-3B;

DETAILED DESCRIPTION

The following description is merely exemplary in nature and is not intended to limit the present disclosure, application, or uses. The devices described herein include an exemplary number of leads, etc. One will understand that the components, including number and kind, may be varied without altering the scope of the disclosure. Also, devices according to various embodiments may be used in any appropriate diagnostic or treatment procedure, including a cardiac procedure.

Figure 1:
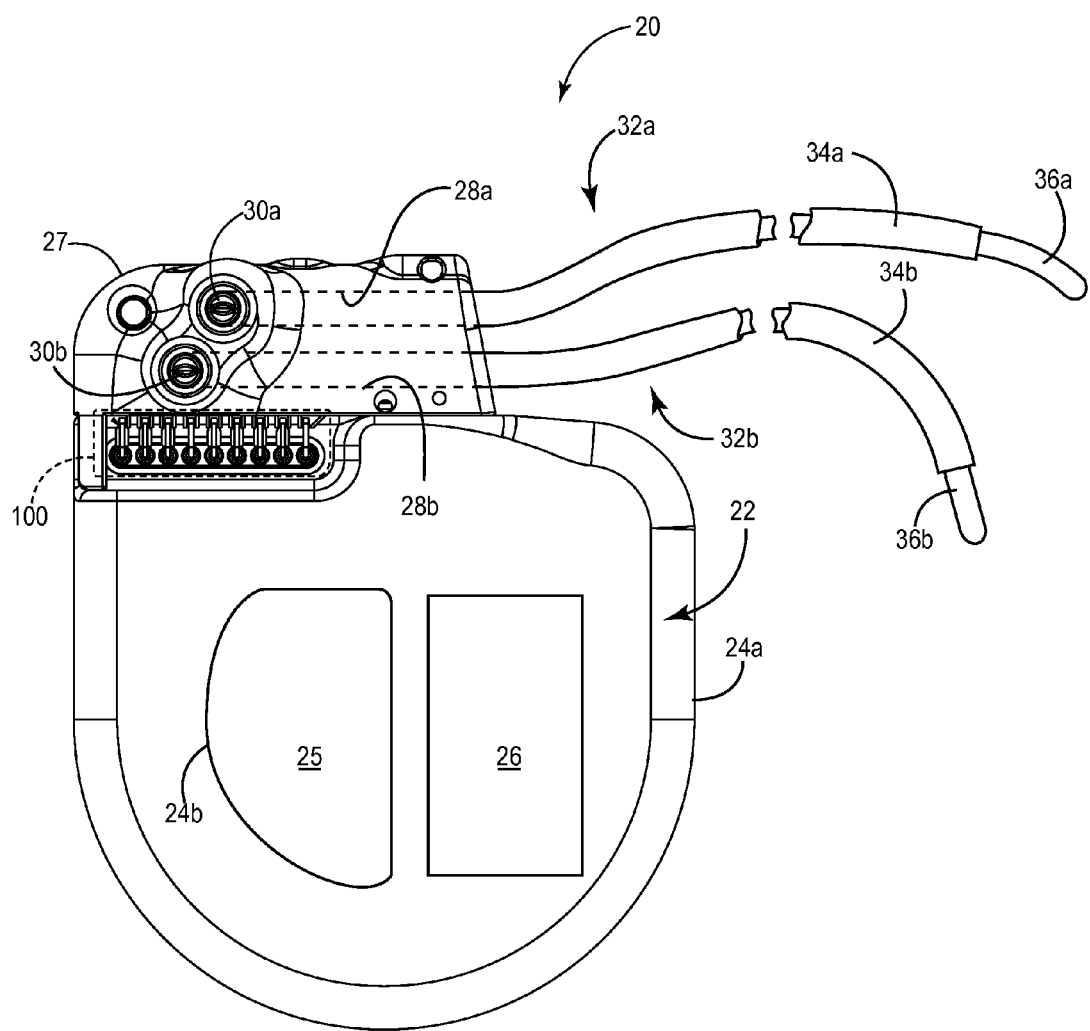
FIG. 1 is a conceptual schematic angled view of an implantable medical device (IMD) in which a medical electrical lead extends therefrom.
Figure 2:
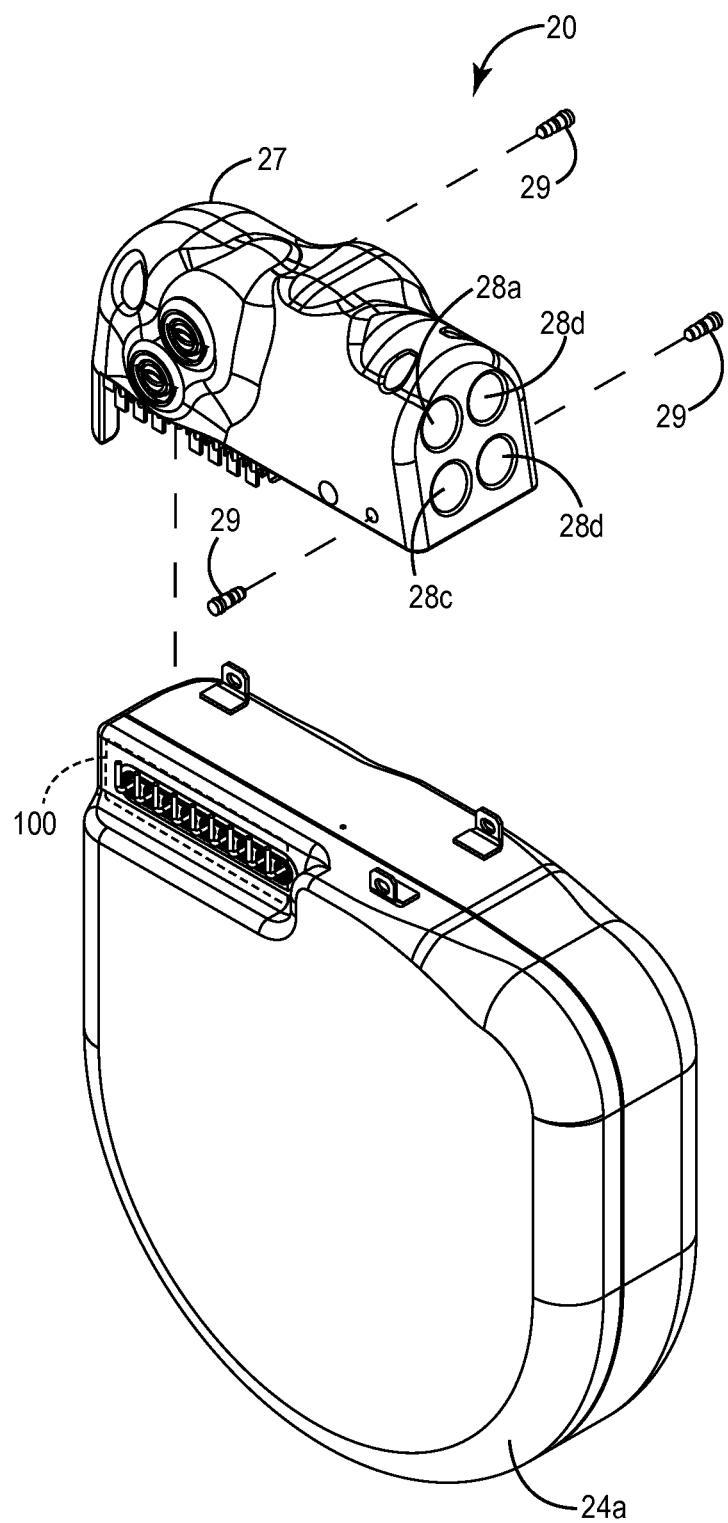
FIG. 2 is a schematic top view of the IMD depicted in FIG. 1.

With reference to FIG. 1, an implantable medical device (IMD) 20 can include implantable pacemakers, implantable cardioverter defibrillator (ICD) devices, cardiac resynchronization therapy defibrillator devices, neurostimulators, drug pumps or combinations thereof. Exemplary IMDs are commercially available as including one generally known to those skilled in the art, such as the Medtronic CONCERTO™, SENSIA™, VIRTUOSO™, RESTORE™, RESTORE ULTRA™, sold by Medtronic, Inc. of Minnesota. IMD 20 can include an implantable case, housing or body assembly 22. Implantable case 22 can be formed of appropriate materials and include appropriate features, such as a hermetically sealed body wall 24a. Body wall 24a comprises substantially conductive material such as titanium.

Contained within or associated with case 22 can be a power device 25 such as one or more batteries and/or capacitors encased in housing or case body wall 24b, a controller assembly 26, and a connector body 27. Controller assembly 26 can include a circuit board having a processor, memory, transmitter, receiver, and/or other appropriate portions. Connector body 27 can extend from or be integrated with case 22. At its distal end, connector body 27 can include one or more ports 28a,b that interconnects with one or more connector terminals 30a,b of one or more lead assemblies 32a, b. Exemplary connector bodies 27 can include IS-1 connectors, IS-4 connectors or other suitable connectors. Lead assemblies 32a,b generally include respective lead bodies 34a,b each having a respective tip electrode 36a, b. For example, the first lead assembly 32a can include an active tip electrode 36a and the second lead assembly can include a passive tip electrode 36b.

Figure 3A:
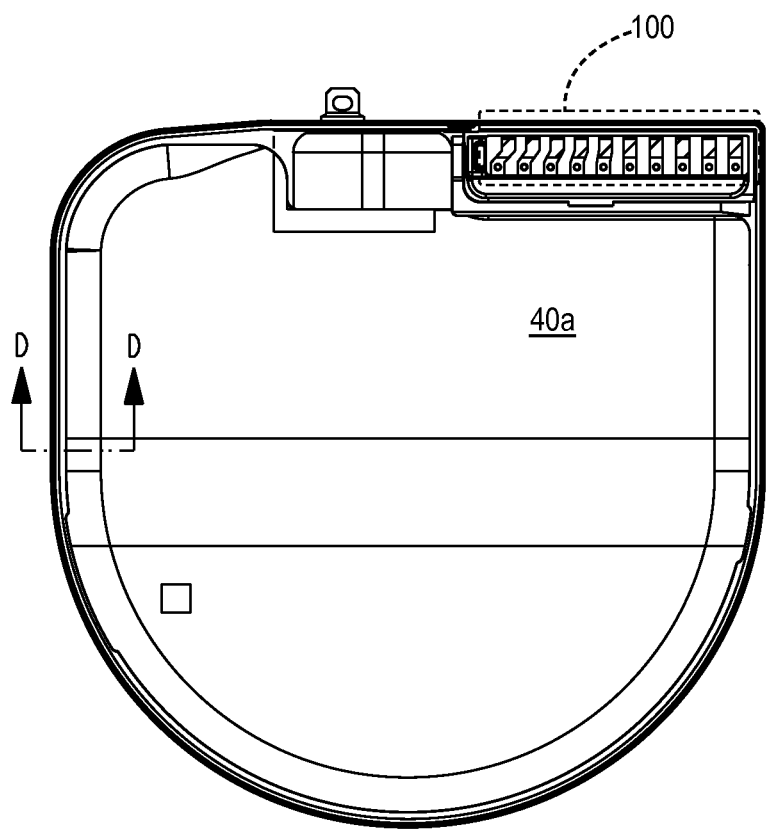
FIG. 3A is a schematic interior view of one side of a housing to an IMD that includes a top side view of a filtered feedthrough electronic module assembly (FFEMA)
Figure 3B:
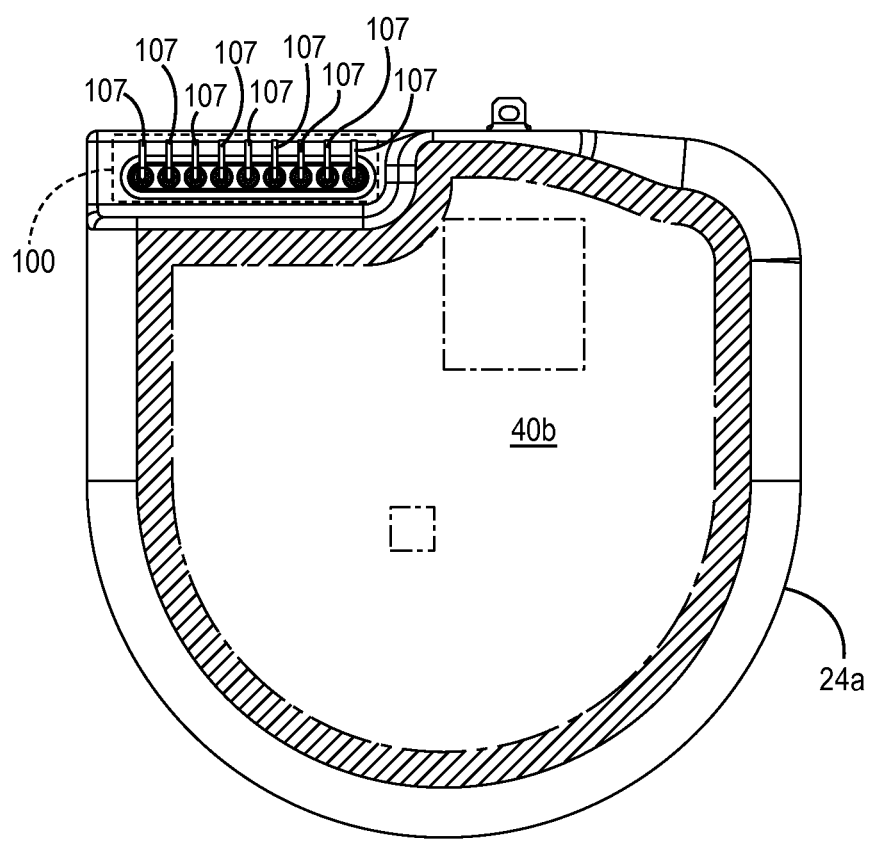
FIG. 3B is a schematic exterior view of the other side of a housing depicted in FIG. 3A to an IMD along with a back side view of a FFEMA.

At its distal end, connector body 27 is connected via set screws 29 to lead assemblies 32a,b. Set screws 29 force lead assemblies 32a,b in place to form an electrical connection via connector body 27, which, at its proximal end, is connected to a filtered feedthrough electronic module assembly (FFEMA) 100, as depicted in FIGS. 3A-5B. FIG. 3A depicts an interior side 40a of housing 24a whereas FIG. 3B shows the flip side or exterior side 40b of the same side of housing 24a. FFEMA 100 electrically connects circuitry, such as a hybrid assembly 162 shown in FIG. 3C, located inside a sealed case of the IMD, to a connector body 27, which connects with external components that extend outside of the housing 24a. FFEMA 100 comprises an electronic module assembly (EMA) 102 connected to a feedthrough assembly 120. The EMA 102 is composed of a non-conductive block, referred to as an electronic module block (EMB) 104, with a set of conductive strips 106 or conductive elements.

EMB 104 is substantially L-shaped; however a variety of suitable shapes can be used. The EMB 104 includes a non-conductive body 102 formed of, for example, silicone, polyurethane and other suitable material. A number of openings or apertures 109 are defined through the body 102 between top and bottom sides. The openings 109 are capable of accepting or receiving feedthrough pins 107 or conductors.

Figure 7:
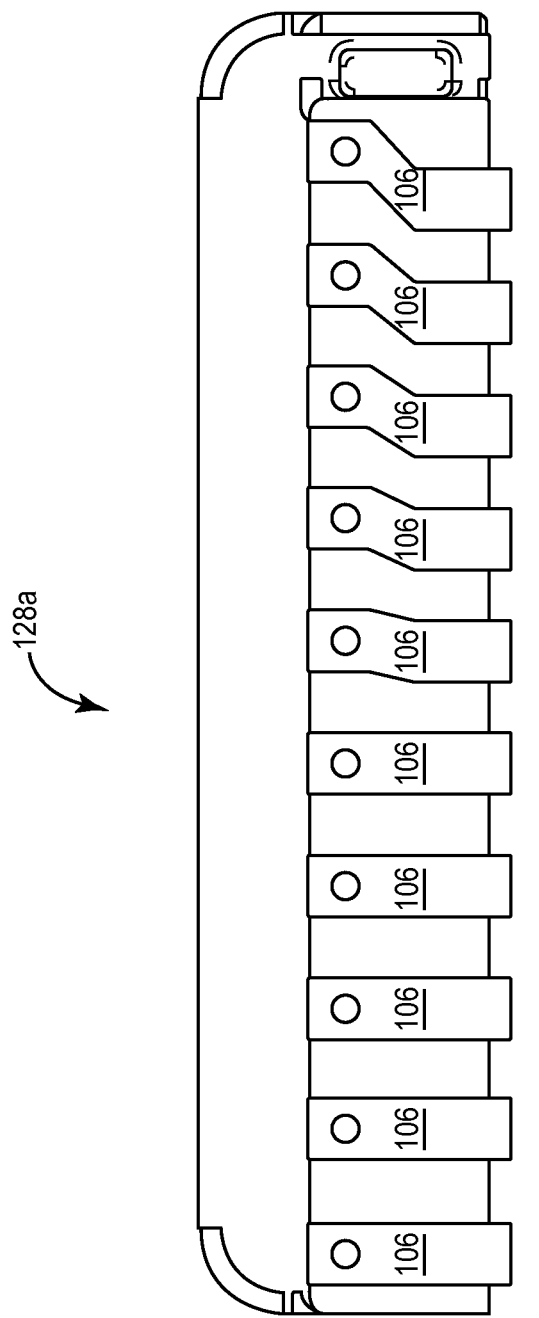
FIG. 7 is a top view of an electronic module block for the FFEMA.

EMB 104 includes a top side 128a, a bottom side 128d, a front side 128b and a back side 128c. Top side 128a, shown in FIG. 7, possesses a flat or substantially flat surface.

A set of conductive strips 106 are electrically and mechanically coupled to the EMB 104 to form EMA 102. In one or more embodiments, each conductive strip 106 possesses a front side and a back side. While the front side of each conductive strip 106 is exposed, the back side conductive strip 106 is directly connected or embedded into the surfaces of the front side 128b, the top side 128a, and the back side 128c; however, the set of conductive strips 106 are not directly placed on the surface of the bottom side 128d. Each conductive strip 106 extends X distance from the top side 128a of the EMB 104 toward the back side 128c. X ranges from about 0.5 millimeters (mm) to about 5.0 mm. The width of each conductive strip 106 portion on the back side 128c can range from about 5 mm to about 25 mm.

A pad 111 or portion of each conductive strip 106 on the back side 128c is used for testing the quality of each conductive strip 106 to conduct current. Pad 111, in one or more embodiments, is seamlessly and/or integrally formed as part of conductive strip 106. In another embodiment, pad 111 can be connected as a separate component to conductive strip 106 through conventional means. Each portion of the conductive strip 106, on the backside of the EMB 104, comprises a thickness that ranges from about 0.5 mm to about 2.0 mm. Each conductive strip 106 is comprised of titanium, gold, nickel or any combination thereof.

Figure 4A:
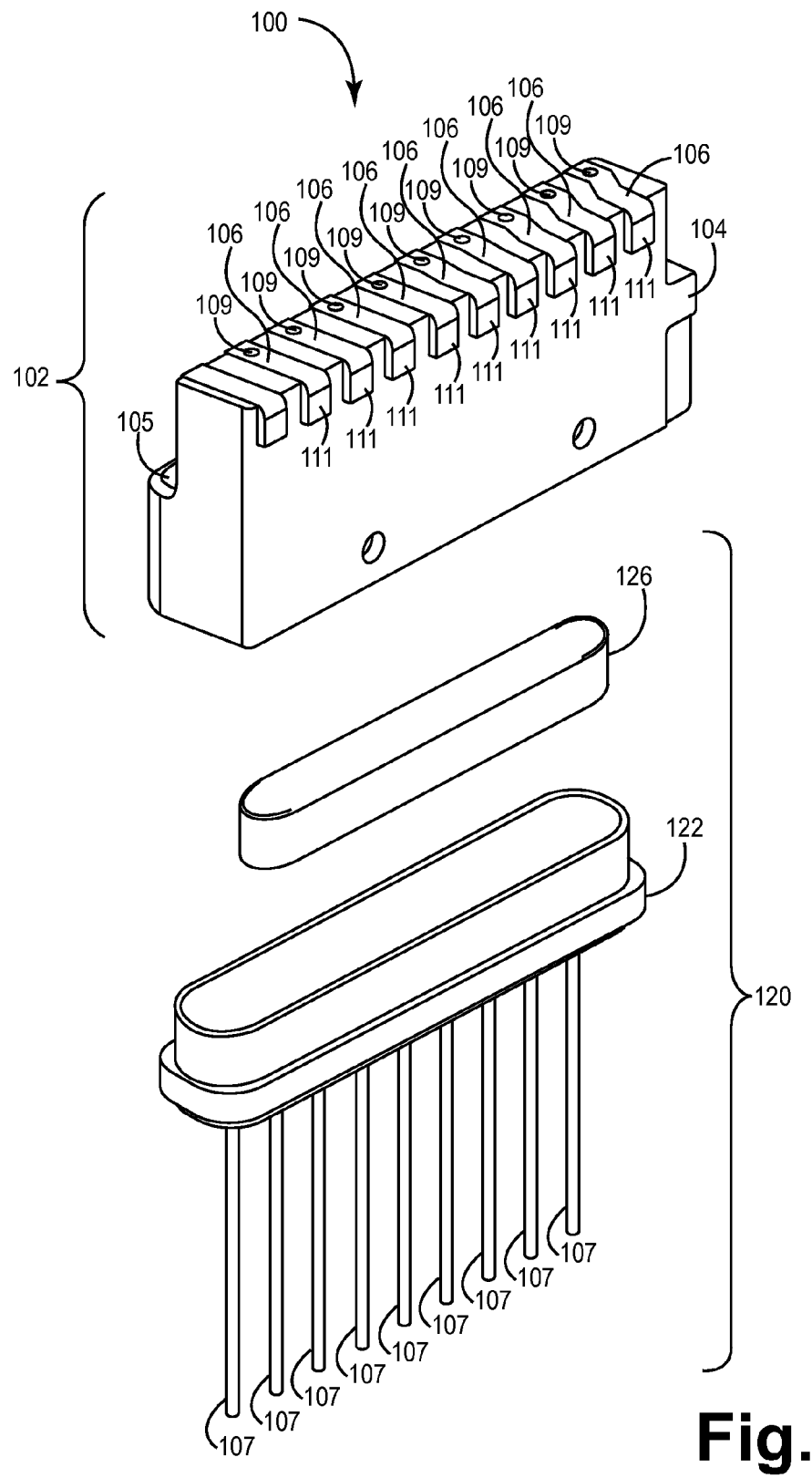
FIG. 4A is a schematic view of components of a FFEMA for the IMD depicted in FIGS. 3A-3C.
Figure 4B:
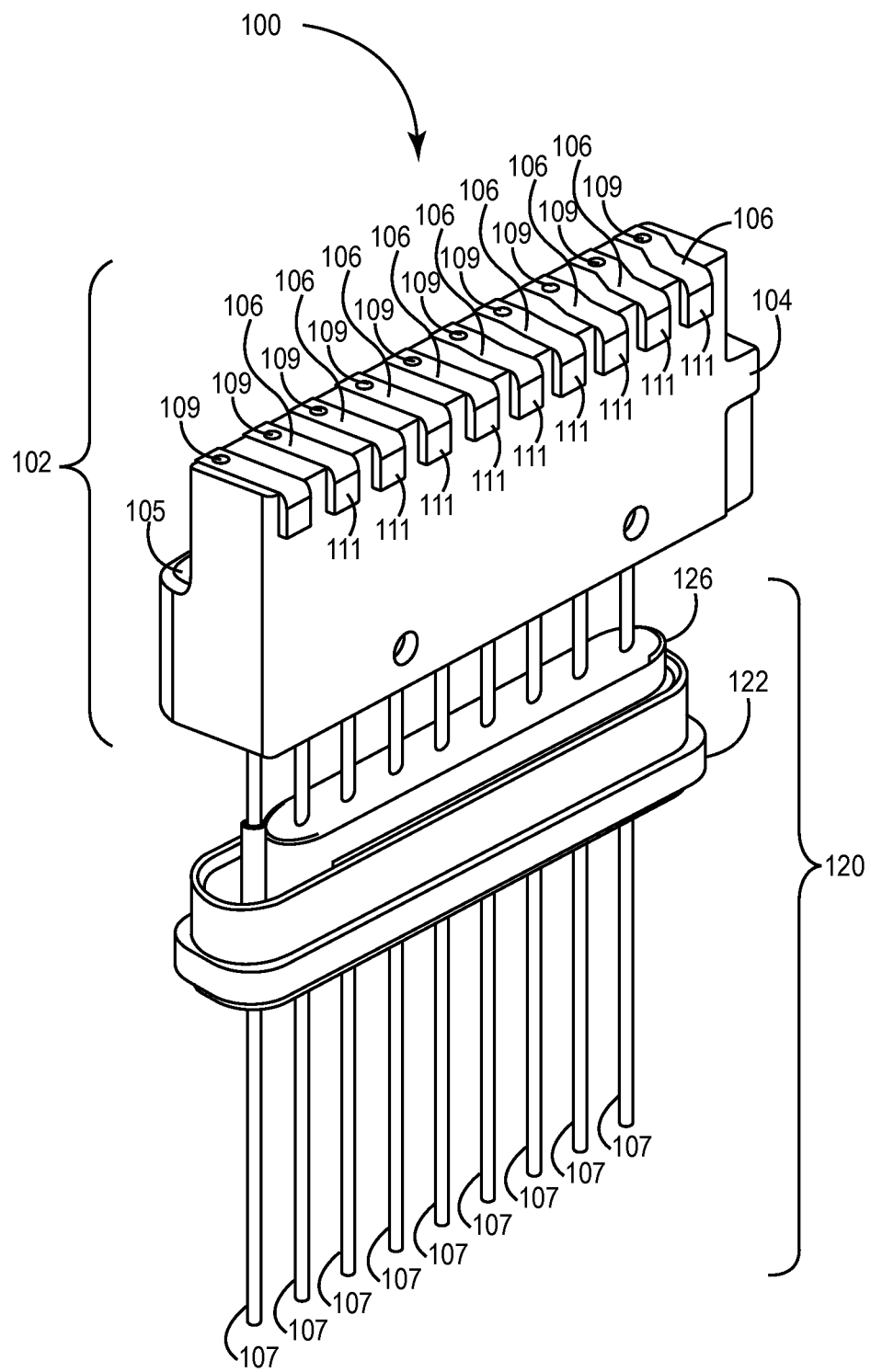
FIG. 4B is a schematic view of an assembled FFEMA for the IMD depicted in FIGS. 3A-3B.
Figure 5A:
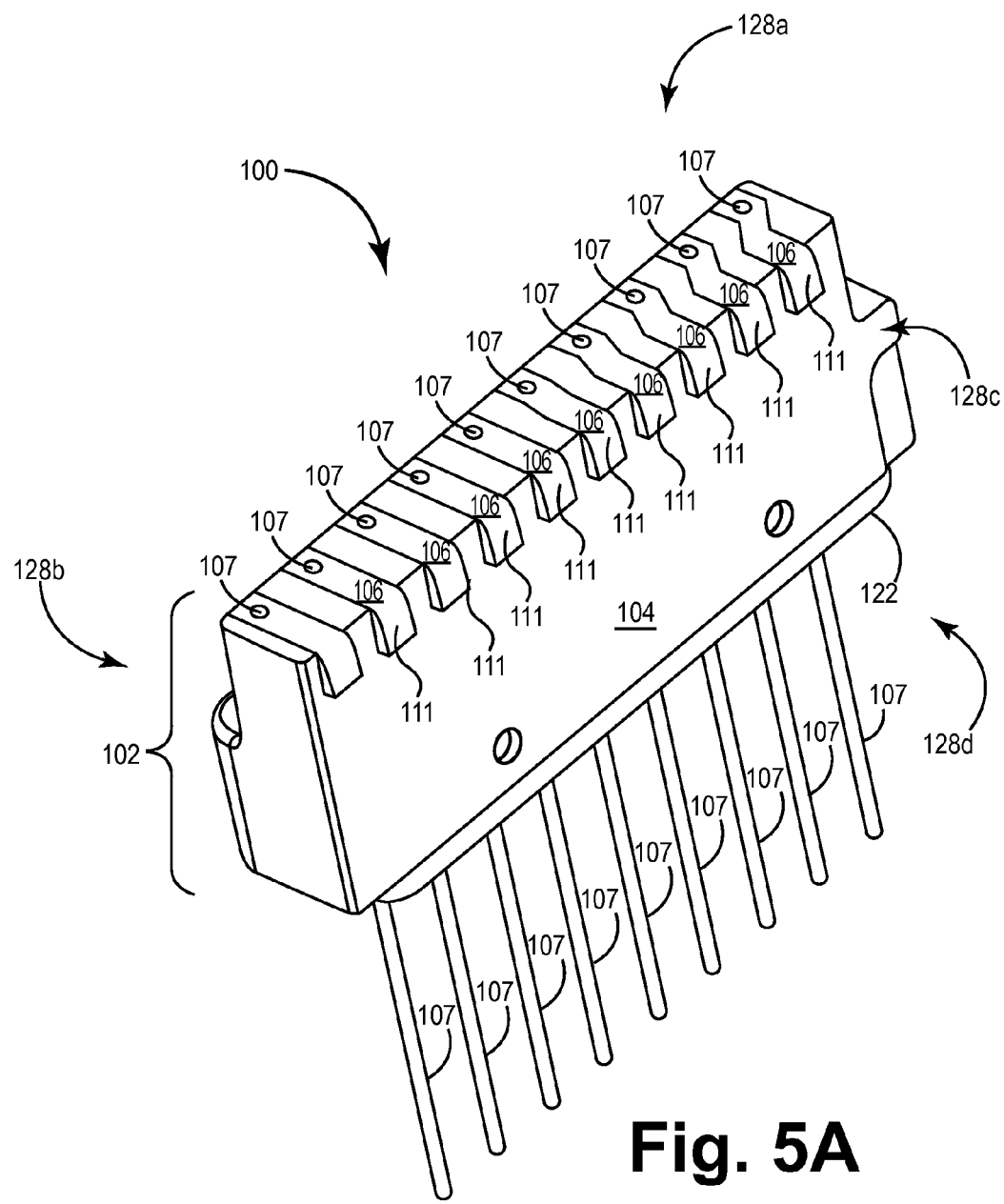
FIG. 5A is a schematic view of a FFEMA for the IMD depicted in FIGS. 3A-3B.
Figure 5B:
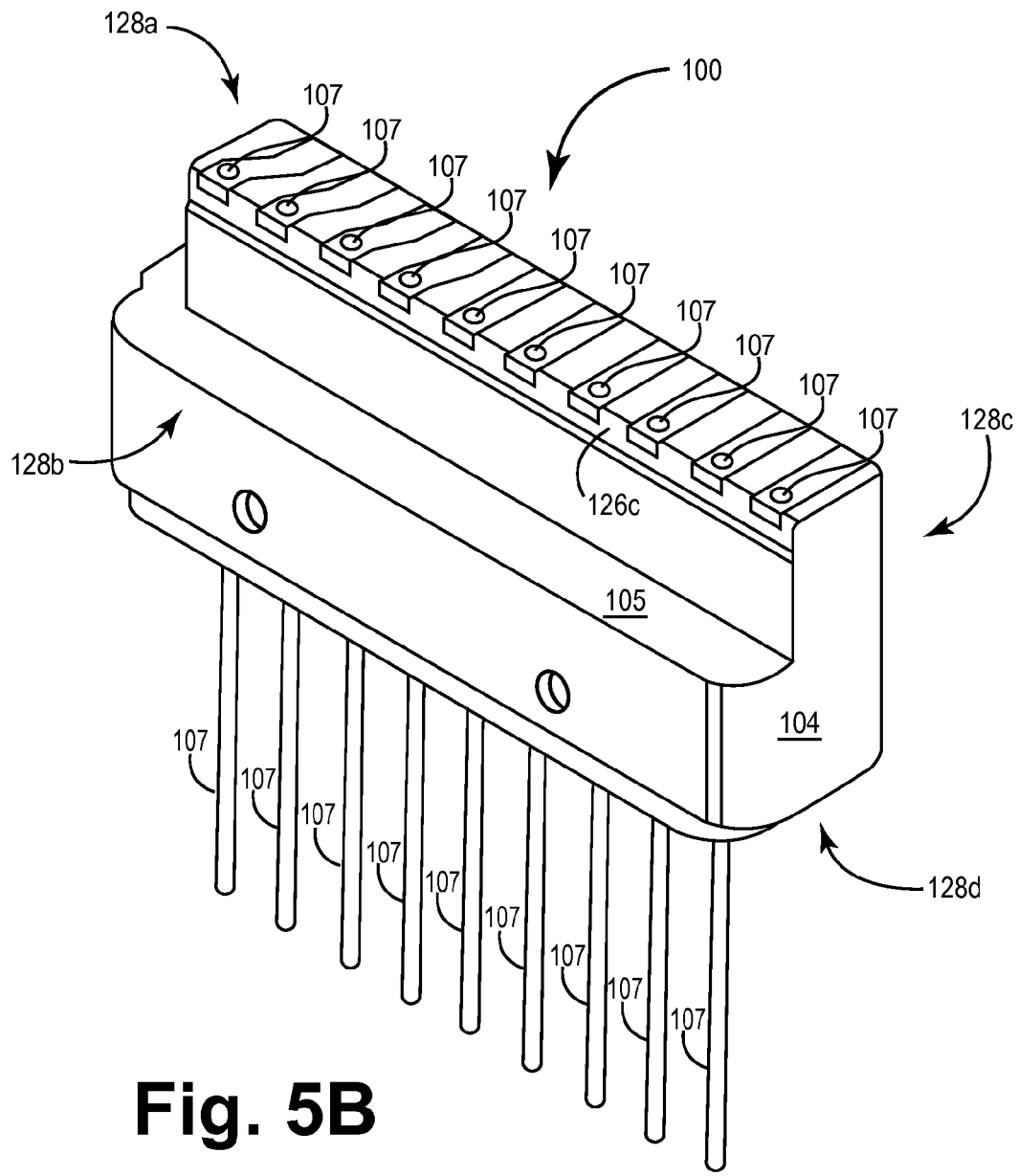
FIG. 5B is a schematic view of a FFEMA for the IMD depicted in FIGS. 3A-3B.
Figure 6:
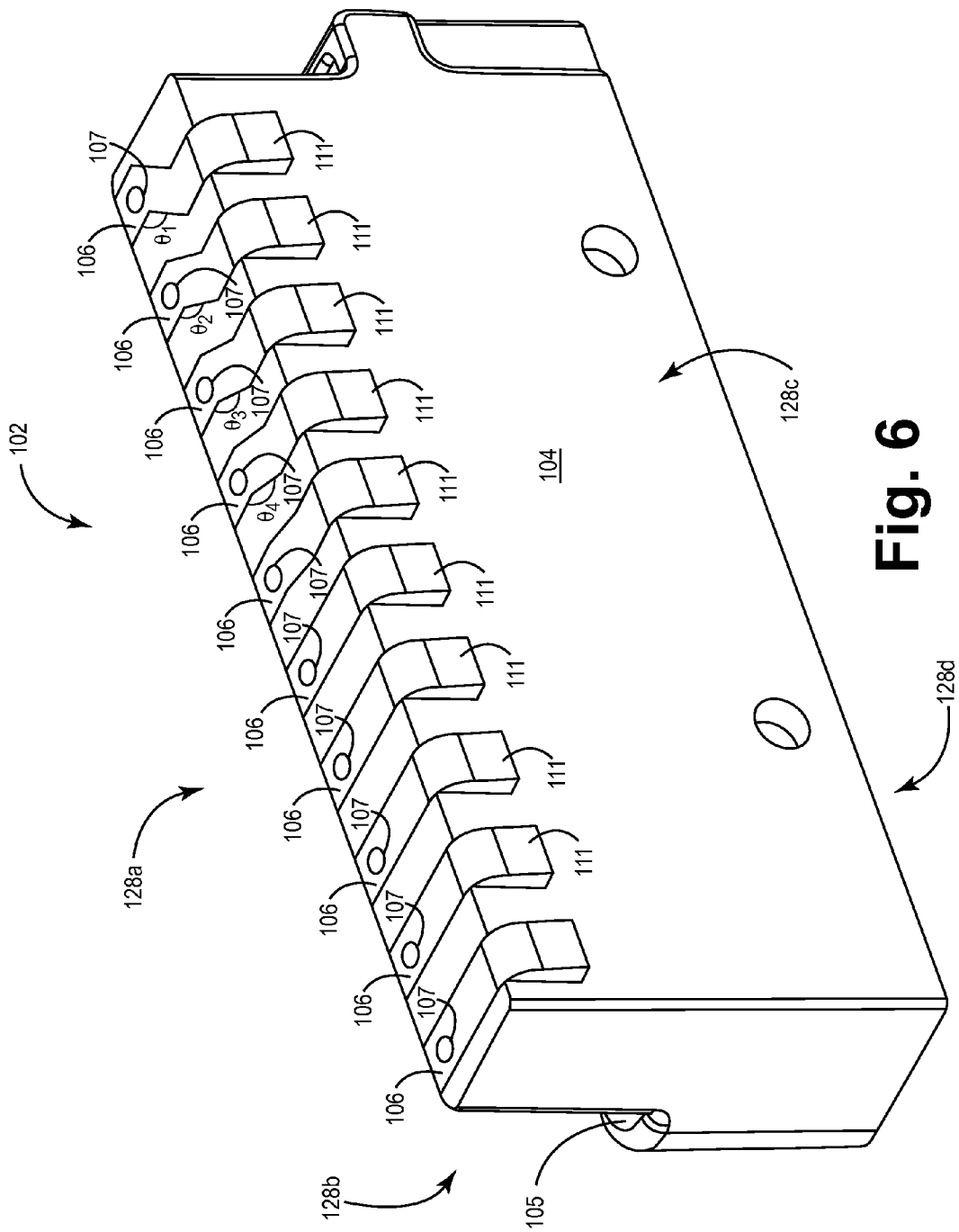
FIG. 6 is an electronic module block of the FFEMA.

Feedthrough assembly 120, depicted in FIGS. 4A-4B, is conventionally formed and connected to EMA 104 in order to form FFEMA 100. Each multipolar feedthrough element 120 includes a feedthrough pins 107, a ferrule 122, a capacitive element 126, an insulator member or element (not shown), and conductive material (not shown) (also referred to as a conductive element). An exemplary multipolar feedthrough element that shows the configuration of the insulator member and conductive material around the pin may be seen with respect to U.S. patent application Ser. No. 12/183,593, filed Jul. 31, 2008 entitled "NOVEL CAPACITIVE ELEMENTS AND FILTERED FEEDTHROUGH ASSEMBLIES FOR IMPLANTABLE MEDICAL DEVICES", and assigned to the assignee of the present invention, the disclosure of which is incorporated by reference in its entirety herein.

Suitable materials for feedthrough members 107 and ferrule 122 can include titanium, niobium, platinum, platinum/iridium, molybdenum, zirconium, tantalum or alloys thereof. The insulator element can comprise an insulative material such as glass, ceramic or other suitable materials. The conductive material can be a conductive epoxy, a conductive polyimide, a conductive solder or other suitable materials. An exemplary conductive epoxy can be Ablebond 8700E commercially available from Ablestik Inc., located in Rancho Dominguez, Calif.; an exemplary conductive polyimide can include Ablebond 71-1 from Ablestik Inc., and exemplary conductive solders can be indium-based, tin-based, gold-based solder, and/or lead based.

The electrically grounded ferrule 122 holds or supports an array of feedthrough pins 107 extending through the ferrule 122. A monolithic discoidal capacitor assembly 126 is positioned around at least some of the feedthrough pins 107. The capacitor assembly 126 is held together by a monolithic body. The capacitor assembly 126 is electrically connected between a feedthrough pin 107 and ground (i.e., to the ferrule 122) to provide low-pass electromagnetic interference (EMI) filtering. An EMA block 104 can be positioned over the feedthrough pin 107 and the discoidal capacitor assembly 126. Feedthrough pins 107 pass through the holes 109 in the conductive strips 106 on the EMB 104. Feedthrough pins 107 are then trimmed flush to the conductive strips 106 and laser welded such that the trimmed pins 107 make an electrical connection to the conductive strips 106. Thereafter, as shown in FIG. 3C, a conductive ribbon 160 or weld connects one or more feedthrough pins 107 to one or more corresponding bond pads 166 on a hybrid assembly or circuit board 162.

Figure 8:
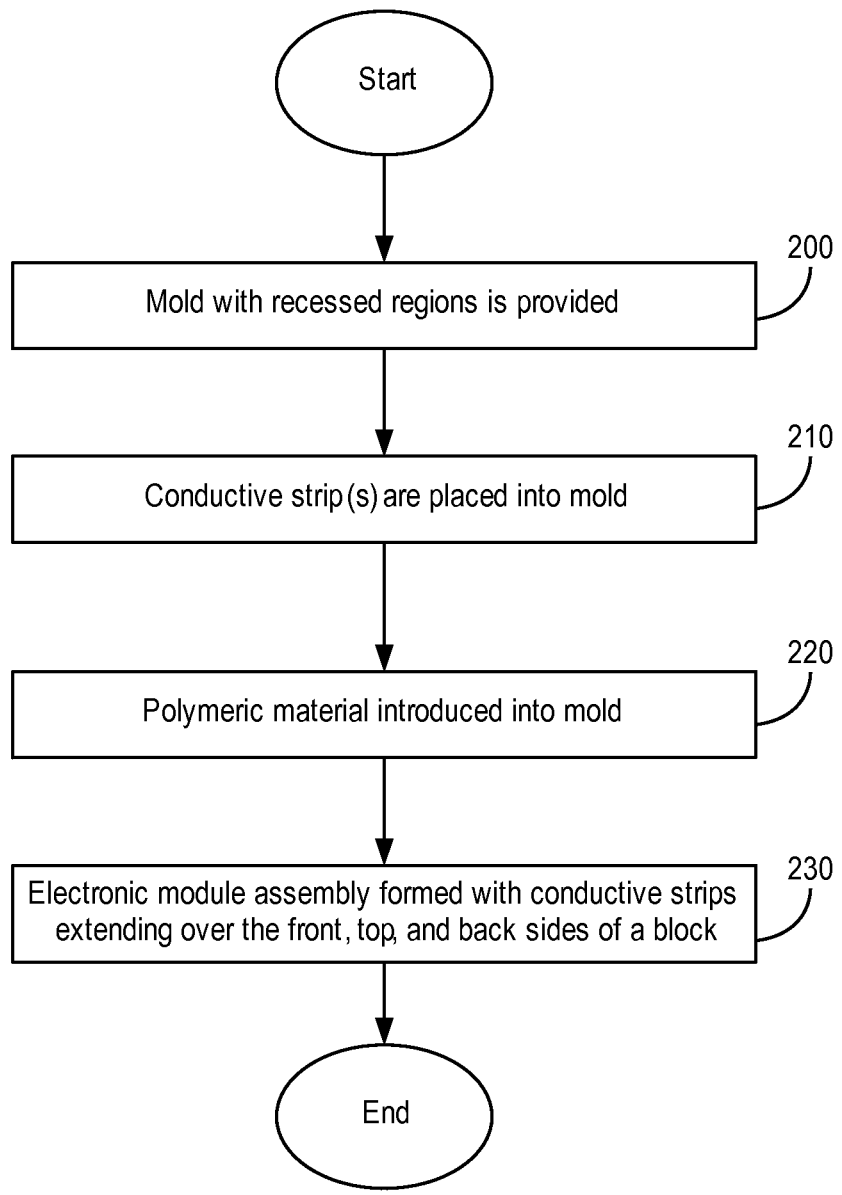
FIG. 8 depicts a flow diagram for forming an EMA.

FIG. 8 depicts a method of forming an EMA 104. At block 200, a mold (not shown) is provided that is configured to form a non-conductive block or EMB 102 with a top side, a back side, a front side, and a bottom side. The mold possesses features that provide a surficial mirror image of EMB 102. The first side of the mold forms the top side of the non-conductive block, the second side of the mold forms the back side of the non-conductive block, and the third side of the mold forms the front side of the mold. Non-conductive block does not conduct current. The front side is directly adjacent to the top side and the top side is directly adjacent to the back side of the non-conductive block. In one or more embodiments, a polymer such as silicone, polyurethane, polyetherimide, and/or poly ether ketone can be used to form EMB 102. A 10-30% glass filled polyetherimide is commercially available under the tradename Ultem from General Electric located in New York. At block 210, a plurality of conductive strips are placed in the mold at a first side, a second side and a third side of the mold. Each conductive strip is formed of titanium or nickel and plated and/or sputtered with gold and/or platinum to provide a low resistance path. At block 220, a polymeric material such as silicone and/or polyurethane is introduced into the mold. At block 230, the EMA is formed such that the non-conductive block has a top side, a back side, a front side, and a bottom side. Each conductive strip extends from the front side over the top side onto the back side of the non-conductive block.

After EMA 102 has been formed, EMA 102 is tested, for example, to ensure that conductive strips 106 properly function. An exemplary testing system may be seen with respect to U.S. patent application Ser. No. 11/236,369, filed Sep. 27, 2005 entitled "Determination of Equivalent Series Resistance", and assigned to the assignee of the present invention, the disclosure of which is incorporated by reference in its entirety herein. The testing system described herein includes a testing fixture with a set of pogo pins. EMA 102, the device under test, is secured beneath the test fixture's set of pogo pins. The pogo pins move toward the pads 111 of conductive strips 106 until contacting the pads 111. A current is passed through each pogo pin through to pads 111. If current passes through each conductive strip 106, the conductive strips 102 of the EMA 102 pass its quality inspection for functionally being able to pass current. If one or more conductive strips 102 cannot pass current, the EMA 102 fails its quality inspection and is not used in the formation of a FFEMA for an IMD. Since the pogo pins no longer contact the conductive strips 106 on the top side 126b of EMA 102, the surface of the conductive strips 106 remains intact. By preventing any nicks or gouges associated with test probes to the surface of the conductive strips 106, a pristine surface on the conductive strips 106 is maintained for subsequent processes such as laser ribbon bonding, wire bonding or other suitable operations. Additionally, it is more likely that EMA 102 will pass the quality inspection related to conducting current through the conductive strips 106. In turn, the cost of an IMD is reduced for patients.

Although the present invention has been described in considerable detail with reference to certain disclosed embodiments, the disclosed embodiments are presented for purposes of illustration and not limitation and other embodiments of the invention are possible. It will be appreciated that various changes, adaptations, and modifications may be made without departing from the spirit of the invention and the scope of the appended claims. For example, while one method for forming EMB 104 involves the use of a mold, it should be appreciated that numerous methods may be used to form EMA 102 without a mold. For example, EMB 104 could be extruded or formed through any conventional means. Additionally, the conductive strips can be coupled to the EMB 104 through hot pressing each strip into EMB 104, or using an adhesive to connect each strip to EMB 104.

What is claimed is:

1. An implantable medical device (IMD) comprising:
a housing;
a connector module coupled to the housing;
a filtered feedthrough electronic module assembly (FFEMA) coupled to the connector module and to the housing, the FFEMA comprises:
a filtered feedthrough assembly that includes a set of feedthrough pins;
an electronic module assembly (EMA), the EMA comprises:
an electronic module block (EMB) having a top side, a bottom side, a front side and a back side;
a set of conductive strips correspondingly directly conductively coupled to the set of feedthrough pins, wherein each conductive strip being directly coupled to the front side, the top side, and the back side of the EMB;
at least one conductive connector being coupled to at least one feedthrough pin and a hybrid assembly,
wherein a portion of each conductive strip that extends to the back side of the EMB is configured as a test pad for testing the conductivity of each conductive strip.

2. The IMD of claim 1, wherein each conductive strip extends from the top side of the EMB toward the back side from about 0.5 millimeters (mm) to about 5 mm.

3. The IMD of claim 2, wherein each conductive strip seamlessly extending along surfaces of the front side, the top side, and the back side of the EMB.

4. The IMD of claim 3, wherein at least a portion of each conductive strip is exposed at the front side of the EMB.

5. The IMD of claim 4, wherein each conductive strip being embedded into the front side, the top side and the backside of the EMB.

6. The IMD of claim 1, wherein each conductive strip, on the backside of the EMB, comprising a thickness that ranges from about 0.5 mm to about 2 mm.

7. The IMD of claim 1, wherein each conductive strip being comprised of one of titanium, nickel, aluminum, copper, niobium, and tantalum.

8. The IMD of claim 7 wherein each conductive strip being plated with at least one of gold and platinum.

9. The IMD of claim 1, wherein the EMB comprises a polymer selected from the group consisting of silicone, polyurethane, and poly ether ether ketone or combinations thereof.

10. The IMD of claim 1, wherein the top side being directly adjacent to the back side and the front side of the EMB.

11. The IMD of claim 1, wherein each feedthrough pin being laser welded to each corresponding conductive strip.

12. The IMD of claim 1, wherein one of gold, platinum and copper introduced over at least one surface of at least one conductive strip to provide a low resistive path between the feedthrough pin and the hybrid assembly.

13. An electronic module assembly (EMA) for an implantable medical device, the EMA comprising:
a non-conductive block having a top side, a bottom side, a front side and a back side;
a plurality of conductive strips coupled to the non-conductive block, each conductive strip having a front side and a back side, the back side of each conductive strip extends from the front side across the top side and over to back side of the non-conductive block; and
a plurality of feedthrough pins, wherein each pin of the plurality of feedthrough pins is correspondingly directly conductively connected to a conductive strip of the plurality of conductive strips,
wherein a portion of each conductive strip that extends to the back side of the non-conductive block is configured as a test pad for testing the conductivity of each conductive strip.

14. The EMA of claim 13, wherein the front side of each conductive strip is exposed.

15. The EMA of claim 13, wherein each conductive strip extends from the top side of the non-conductive block toward the bottom side from about 0.5 millimeters (mm) to about 5 mm.

16. A method of forming an EMA for an implantable medical device comprising:
providing a mold configured to form a non-conductive block with a top side, a bottom side, a front side, and a back side;
placing a plurality of conductive strips at a first side, a second side and a third side of the mold, the first side of the mold forms the top side of the non-conductive block, the second side of the mold forms the back side of the non-conductive block, and the third side of the mold forms the front side of the mold;
introducing a polymeric material into the mold;
forming the EMA comprising the non-conductive block having a top side, a back side, a front side, and a bottom side, each conductive strip extending seamlessly from the front side over the top side onto the back side of the non-conductive block, wherein each conductive strip is configured to be directly conductively connected to a pin associated with a plurality of pins, wherein a portion of each conductive strip that extends to the back side of the non-conductive block is configured as a test pad for testing the conductivity of each conductive strip.

17. The method of claim 16, wherein the front side is directly adjacent to the top side and the top side is directly adjacent to the back side of the non-conductive block.

18. A method of forming an EMA for an implantable medical device comprising:

forming a non-conductive block with a top side, a bottom side, a front side, and a backside; and coupling a plurality of conductive strips to the non-conductive block, wherein each conductive strip being coupled to the top side, the bottom side and the front side of the non-conductive block wherein the plurality of conductive strips is configured to directly conductively connected to a plurality of pins, wherein a portion of each conductive strip that extends to the bottom side of the non-conductive block is configured as a test pad for testing the conductivity of each conductive strip.

19. An EMA for an implantable medical device comprising:

means for forming a non-conductive block with a top side, a bottom side, a front side, and a backside;

means for coupling a plurality of conductive elements to the non-conductive block, wherein each conductive element being coupled to the top side, the bottom side and the front side of the non-conductive block and the plurality of conductive elements is configured to directly conductively connect to a plurality of pins, wherein a portion of each conductive strip that extends to the bottom side of the non-conductive block is configured as a test pad for testing the conductivity of each conductive strip.

* * * * *